United States Patent [19]

Lyell

[11] Patent Number: 5,348,541
[45] Date of Patent: Sep. 20, 1994

[54] SUPRAPUBIC CATHETER PLACEMENT APPARATUS (LYELL SOUND)

[76] Inventor: Mark S. Lyell, 1304 Roswell, Pascagoula, Miss. 39581

[21] Appl. No.: 56,532

[22] Filed: May 5, 1993

[51] Int. Cl.$^5$ ............................................. A61M 5/178
[52] U.S. Cl. .................................. 604/164; 604/272; 604/280; 606/205
[58] Field of Search ................. 128/657, 772; 604/164, 604/264, 272, 280; 606/205, 206, 209

[56] References Cited

U.S. PATENT DOCUMENTS

| | | | |
|---|---|---|---|
| 2,541,246 | 2/1951 | Held | 606/205 |
| 3,630,198 | 12/1971 | Henkin | 128/215 |
| 3,860,006 | 1/1975 | Patel | 128/347 |
| 3,908,637 | 9/1975 | Doroshow | 128/2 |
| 4,174,715 | 11/1979 | Hasson | 606/206 |
| 4,684,369 | 8/1987 | Wildemeersch | 604/272 |
| 4,762,519 | 8/1988 | Frimberger | 604/280 |
| 4,826,481 | 5/1989 | Sacks et al. | 604/54 |
| 4,873,977 | 10/1989 | Avant et al. | 128/334 |
| 4,932,413 | 6/1990 | Shockey et al. | 128/657 |
| 5,152,749 | 10/1992 | Giesy et al. | 604/164 |
| 5,176,700 | 1/1993 | Brown et al. | 606/206 |

FOREIGN PATENT DOCUMENTS 2454371 6/1975 Fed. Rep. of Germany ...... 606/205

*Primary Examiner*—Max Hindenburg
*Attorney, Agent, or Firm*—Wenderoth, Lind & Ponack

[57] ABSTRACT

A surgical apparatus is provided for placing a suprapubic catheter within the bladder of a patient. The apparatus essentially includes an elongate element defining a hollow tube and having an end for insertion through the urethra, a flexible wire disposed within the elongate element extending along the length of the elongate element, and a means for reciprocating the flexible wire such as a spring within the elongate element. The end of the flexible wire at the insertion end of the apparatus is provided with a coupling such as a hook for coupling the flexible wire to a catheter tip. The other end of the flexible wire at the handle end of the apparatus is operatively connected to the reciprocating means. The handle has two positions, the first position being a position when the coupling of the flexible wire projects from the end of the apparatus to allow for coupling with the catheter tip, the second position being a position when the catheter is coupled with the apparatus and is retracted within the end of the apparatus.

7 Claims, 3 Drawing Sheets

SOUND IS PUSHED THROUGH ABDOMINAL WALL

CATHETER IS PLACED INSIDE SOUND AND HELD WITH HOOK
CAP IS REMOVED BEFORE CATHETER PLACED

CATHETER PULLED INTO BLADDER, RELEASED FROM SOUND BALLOON, INFLATED TO HOLD IN BLADDER, SOUND REMOVED

SUPRAPUBIC CATHETER PLACEMENT APPARATUS (LYELL SOUND)

BACKGROUND OF THE INVENTION

1. Field of the Invention

The present invention relates to a surgical apparatus for placement of a catheter within a body cavity. More particularly, the invention relates to an apparatus and method for placement of a suprapubic catheter within the bladder.

2. Description of Related Art

Suprapubic catheters and instruments are used in many clinical settings where continuous bladder drainage is desired. Suprapubic catheterization offers a number of advantages over transurethral catheterization, especially for long term catheterization, such as increased patient comfort, minimized infection, improved irrigation and drainage, etc.

Current methods for placing suprapubic catheters essentially fall into two categories, those employing an "outside-to-inside" technique and those employing an "inside-to-outside" technique.

The outside-to-inside technique for suprapubic catheter placement employs the use of a sharp trocar or catheter-obturator combination device. The surgeon pierces the lower abdomen with the trocar or obturator to create a passageway into the bladder. The end of a catheter containing the inlet drain is then inserted through the passageway and positioned in the bladder. Thus as the name implies, the catheter is placed directly into the bladder from outside to inside.

The inside-to-outside technique is less common and employs a grasping device placed in the bladder which is used to pull the catheter end containing the inlet drain into the bladder through a passageway created in the lower abdomen. Initially the surgeon passes the grasping device into the bladder via the urethra and presses the distal end against the bladder dome. A desired penetration site is selected by suprapubic palpitation. The distal end of the grasping device is commonly equipped with a sharp tip capable of piercing through the bladder, facia and abdominal wall. After positioning, the surgeon presses the instrument tip through the bladder, fascia and abdominal wall near the symphysis to create the passageway. The end of a catheter containing the inlet drain is then coupled to the instrument via a coupling mechanism and the catheter is pulled into the bladder. The catheter is released and left in a suprapubic placement.

The grasping device may alternatively possess a blunt tip rather than a piercing tip. A suitable site for passage of the catheter may be determined by palpitation using the blunt tip. An incision may then be extended by the surgeon from the exterior abdominal wall to the bladder to provide a passageway for the instrument advancement. The rest of the procedure may be performed substantially the same as described above using the instrument with a piercing tip.

Several conventional instruments which have been used to place a suprapubic catheter into the bladder using the inside-to-outside technique include the Lowsley retractor, uterine packing forceps, and modified urethral sound.

Other more specialized instruments are also known for placing a suprapubic catheter using the inside-to-outside technique or variations on this technique.

U.S. Pat. No. 5,152,749 to Giesy et al. disclose a surgical apparatus which comprises a needle having a tissue piercing tip, the needle being slidably accommodated within a sheath, and the sheath including a handle means for exposing the tissue piercing tip of the needle. The needle tip also includes or can accommodate a coupling means and a locking means for coupling the catheter to the apparatus.

U.S. Pat. No. 4,684,369 to Wildemeersch disclose a surgical apparatus which comprises a needle having a tissue piercing tip at one end and having an interlocking device for connecting the needle to a catheter at the other end. The tissue piercing tip of the needle is passed through the urethra via a guide means or sheath into the bladder. The needle tip is used to create a passageway through the bladder and abdominal walls, and the needle coupled with the catheter is pulled through the passageway out of the abdomen until the posterior end of the catheter which contains the inlet drain is properly positioned.

There are also known various catheter placement apparatuses for related purposes, such as the apparatuses disclosed in U.S. Pat. No. 4,826,481 to Sacks et al. and U.S. Pat. No. 4,762,519 to Frimberger for placing a feeding tube in the stomach.

SUMMARY OF THE INVENTION

The present invention is designed to provide an improved and simplified device for placement of an instrument such as a catheter within a body cavity. While the present device is especially intended for the placement of suprapubic catheters, it will be apparent to any skilled person in the art that the device may be applied to other medical applications.

The apparatus of the present invention comprises an elongate element defining a hollow tube having a gripping portion for gripping and manipulating the apparatus and a curved portion for insertion through the urethra into the bladder of the patient. The terminal end of the elongate element at the gripping and manipulating portion is defined as the first end, and the terminal end of the elongate element at the curved portion for insertion into the body is defined as the second end.

Disposed within the elongate element is a flexible wire having a length substantially extending from the first end to the second end of the elongate element. The ends of the flexible wire are defined as corresponding to the first and second ends of the elongate element, so that the first end of the flexible wire is that end which terminates at or near to the first end of the elongate element to be gripped, and the second end of the flexible wire is that end which terminates at or near to the second end of the elongate element to be inserted into the body.

The second end of the flexible wire includes a coupling for coupling the flexible wire to a catheter end, particularly to the catheter end containing the inlet drain or opening. The coupling is preferably a hook, more preferably a hook configuration formed in the end of the flexible wire.

The apparatus includes a means for reciprocating the flexible wire within the elongate element. The reciprocating means includes a handle operatively connected to the first end of the flexible wire. When the handle is moved to a first position, the wire is reciprocated within the elongate element so that the second end of the flexible wire projects from the second end of the elongate element for coupling with the catheter tip. When the handle is moved to a second position, the wire is reciprocated back within the elongate element so that the second end of the flexible wire coupled to the catheter tip are retracted within the elongate element.

The reciprocating means is preferably a spring disposed either within the elongate element at a suitable location or outside the elongate element at the first end of the elongate element. In most cases when the reciprocating means is a spring and when the handle is in the first position, the spring will be in a fully compressed condition. When the handle is in the second position, the spring will be in a relaxed condition. The apparatus may be designed so that some compression is maintained on the spring in the second position. This compression may help to retain the coupled catheter within the second end of the elongate member so that the apparatus and catheter miry be easily drawn by the surgeon through the incision into the bladder.

The preferred embodiment of the apparatus includes a removable cap which is removably engageable with the second end of the elongate element. The removable cap is adapted to cover the second end of the elongate element which is inserted through the urethra in order to assist in the passage of the apparatus through the urethra. The cap preferably has a blunt tip portion and a rear portion designed for attachment to the second end of the elongate element. Most preferably the rear portion has an opening or passageway therethrough for coupling with a hook of the flexible wire.

In an alternative embodiment, the elongate element is provided with a recessed inner end wall disposed within the elongate element at the second end. The recessed inner end wall preferably has a slot therein for passing therethrough the flexible wire and coupling.

DETAILED DESCRIPTION OF THE PREFERRED EMBODIMENT(S)

Figure 1:
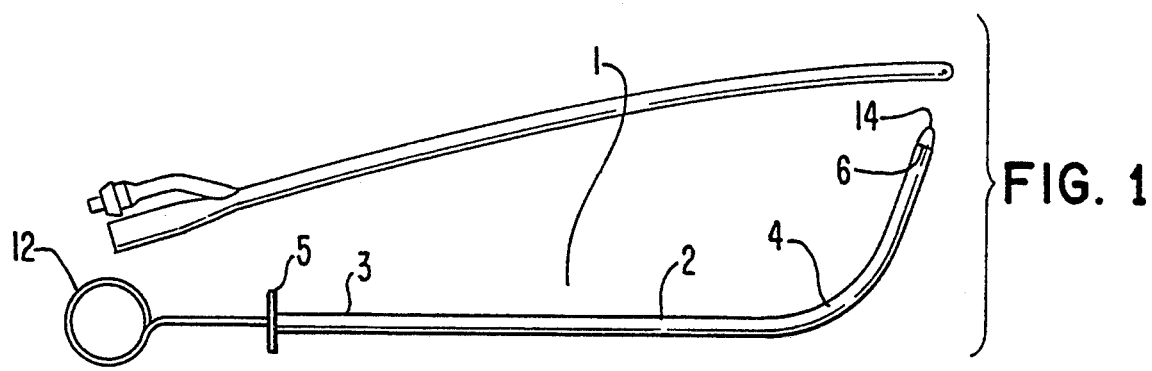
FIG. 1 is a front elevational view of a first embodiment of a catheter placement apparatus according to the present invention.

The preferred embodiment of the surgical apparatus of the present invention for placement of a suprapubic catheter within the bladder of a patient is shown in FIG. 1.

The apparatus 1 comprises an elongate element 2 defining a hollow tube having a gripping portion 3 for gripping and manipulating the apparatus and a curved portion 4 for insertion through the urethra into the bladder of the patient. The terminal end of the elongate element at the gripping and manipulating portion is defined as the first end 5, and the terminal end of the elongate element at the curved portion for insertion into the body is defined as the second end 6.

Figure 2:
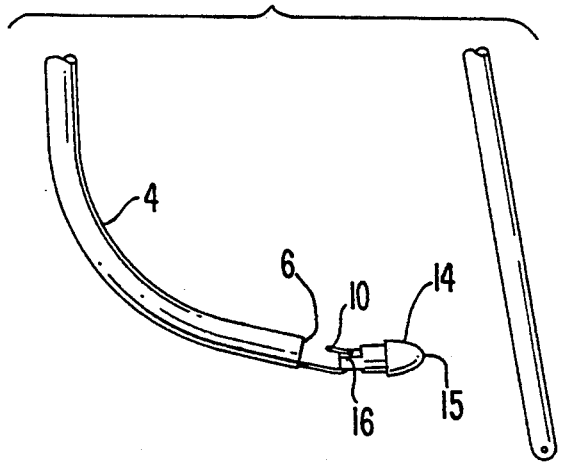
FIG. 2 is a partial exploded front elevational view thereof showing the second end of the elongate element, in particular showing the flexible wire in the first position projecting from the second end of the elongate element, and showing an assembly of a hook coupled to a removable cap.
Figure 3:
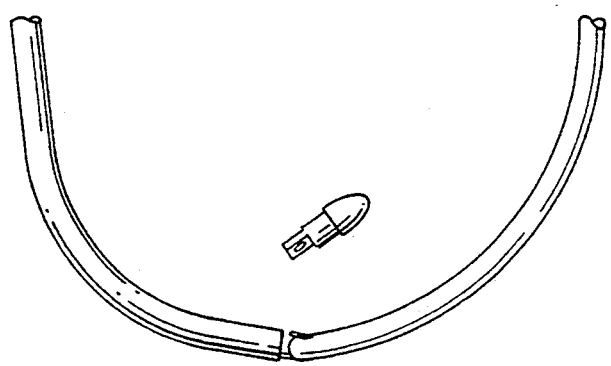
FIG. 3 is a partial exploded front elevational view thereof showing the second end of an elongate element and a catheter tip, in particular showing the flexible wire in a first position projecting from the second end of the elongate element and showing an assembly of a hook coupled to a catheter tip.
Figure 4:
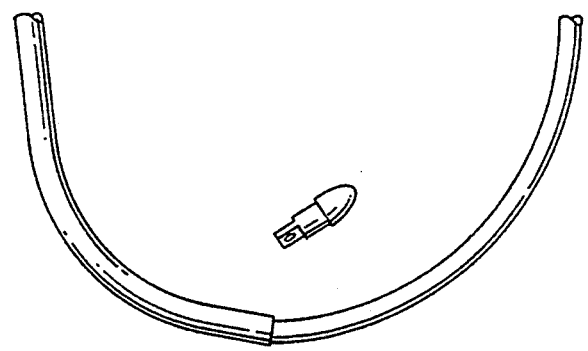
FIG. 4 is a partial exploded front elevational view thereof showing the second end of an elongate element and a catheter tip, in particular showing the flexible wire in a second position, and showing an assembly of the flexible wire and catheter tip retracted within the second end of the elongate element.
Figure 5:
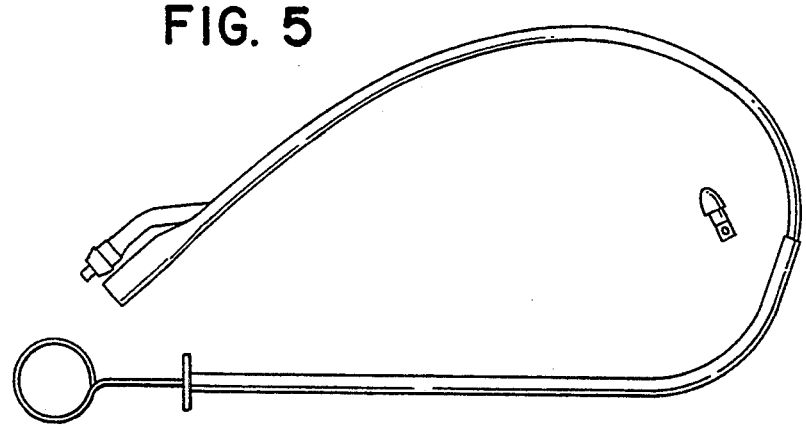
FIG. 5 is a front elevational view thereof showing an assembly of the suprapubic catheter placement apparatus of the present invention coupled to a catheter.
Figure 6A:
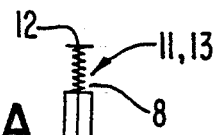
FIG. 6 is an illustration showing the internal structure of a second embodiment of the catheter placement apparatus of the present invention taken from a front elevational view, showing an external spring reciprocating means and a different handle.
Figure 6B:
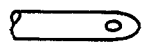
Figure 7A:
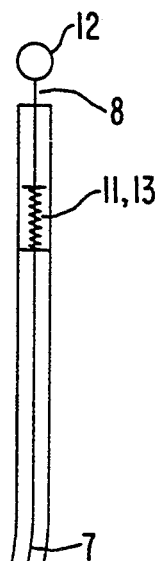
FIG. 7 is an illustration showing the internal structure of a third embodiment of the catheter placement apparatus of the present invention taken from a front elevational view, showing an internal spring reciprocating means and showing an alternative structure of the second end having a recessed inner end wall and a slot.
Figure 7B:
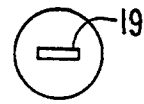
Figure 5:
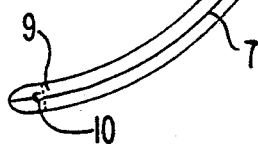
Figure 5:

As shown in FIGS. 6 and 7, disposed within the elongate element is a flexible wire 7 having a length substantially extending from the first end to the second end of the elongate element. The ends of the flexible wire are defined as corresponding to the first and second ends of the elongate element, so that the first end 8 of the flexible wire is that end which terminates at or near to the end of the elongate element to be gripped, and the second end 9 of the flexible wire is that end which terminates at or near to the end of the elongate element to be inserted into the body. The second end of the flexible wire includes a coupling 10 for coupling the flexible wire to the catheter tip. The coupling is preferably a hook and more preferably is a hook formed in the end of the flexible wire as shown in FIG. 2.

The apparatus includes a means for reciprocating 11 the flexible wire within the elongate element. The reciprocating means includes a handle 12 operatively connected to the first end of the flexible wire. When the handle is moved to a first position, the wire is reciprocated within the elongate element so that the second end of the flexible wire projects from the second end of the elongate element for coupling with the catheter tip. When the handle is moved to a second position, the wire is reciprocated back within the elongate element so that the second end of the flexible wire and the catheter tip are retracted within the elongate element.

The reciprocating means is preferably a spring 13 disposed either within the elongate element or outside the elongate element at the first end of the elongate element. See FIGS. 6 and 7. Thus when the handle is in the first position, the spring is in a fully compressed condition, and when the handle is in the second position, the spring is relaxed or under some compression. The apparatus may be designed so that the surgeon need only apply hand pressure to the handle to move the handle to the second position and project the coupling from the second end. When hand pressure is released the apparatus can be designed to automatically return the handle to the first position thereby automatically retracting the coupling within the second end.

The preferred embodiment of the apparatus includes a removable cap 14 which is removably engageable with the second end of the elongate element. The removable cap is adapted to cover the second end of the elongate element to assist in the easy passage of the curved portion of the apparatus through the urethra. The cap preferably has a blunt tip portion 15 and a rear portion 16 designed for attachment to the elongate element. Most preferably the rear portion has an opening or passageway 17 therethrough for coupling with a hook in the flexible wire.

In an alternative embodiment, the elongate element is provided with a recessed inner end wall 18 disposed within the elongate element at the second end. The recessed inner end wall preferably has a slot 19 therein for passing therethrough the flexible wire and coupling when the coupling is disengaged. See FIG. 7.

The elongate element may be composed of any suitable rigid material. Preferably the elongate element is composed of a rigid plastic or metal. The handle, flexible wire and reciprocating means may be constructed from any suitable known material. The apparatus may be economically manufactured and sold in sterile packaging, as a disposable instrument, and in a disposable set or kit with a suitable catheter. The apparatus of the invention may be designed to use with most conventional catheters.

In summary, the apparatus of the present invention provides a simplified construction of an apparatus for placing a suprapubic catheter within a bladder.

In practice, a suprapubic catheter is placed within the bladder according to the following method, with reference to the figures.

Figure 8:
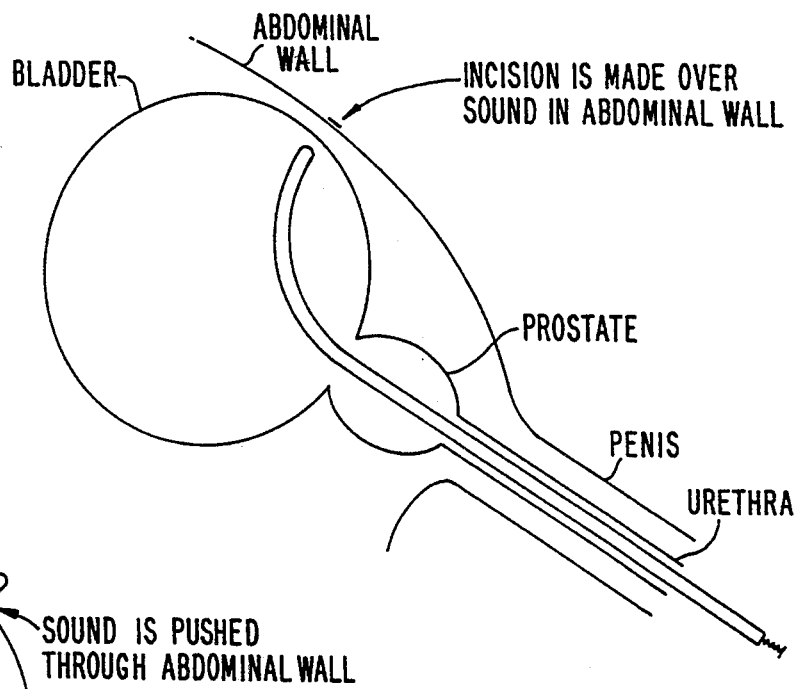
FIGS. 8 to 11 are illustrations showing the method of placing a suprapubic catheter in a bladder using a catheter placement apparatus according to the present invention.
Figure 9:
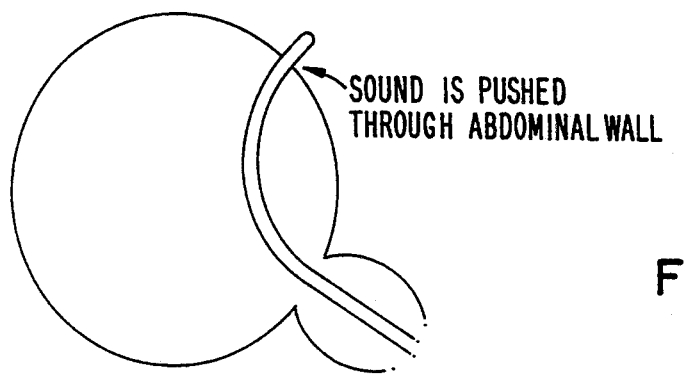
Figure 10:
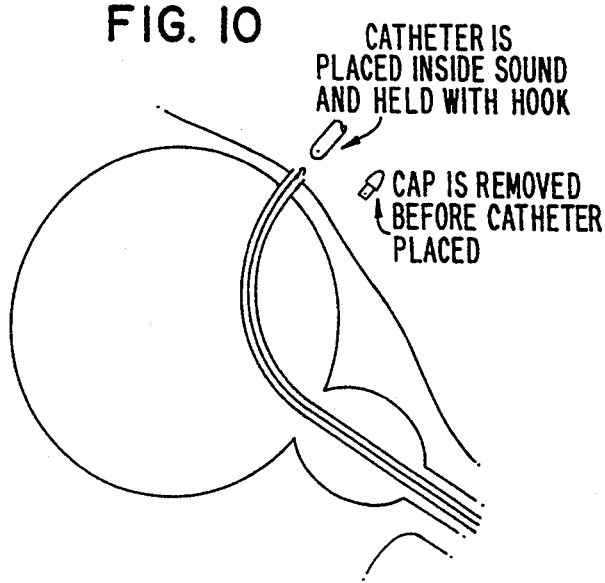

As illustrated in FIG. 8, the curved portion of the elongate element is initially inserted through the urethra into the bladder while the handle is in the second position, i.e. the flexible wire is fully retracted within the elongate element. The second end of the elongate element is pressed against the bladder and abdominal walls. The surgeon selects an incision point by suprapubic palpitation. An incision is extended by the surgeon through the abdominal wall, fascia and bladder near the symphysis. Then the second end of the elongate element is pushed through the incision as shown in FIG. 9.

The handle is then moved to the first position, so that the flexible wire and coupling project from the second end of the elongate element. The catheter tip is coupled with the coupling to the apparatus. If the apparatus includes a removable cap, the cap must first be disengaged from the coupling before the catheter tip is engaged, as shown in 10. Upon coupling the catheter to the wire, the handle is moved to the second position. This retracts the coupling together with the catheter tip within the second end of the elongate element.

Figure 11:
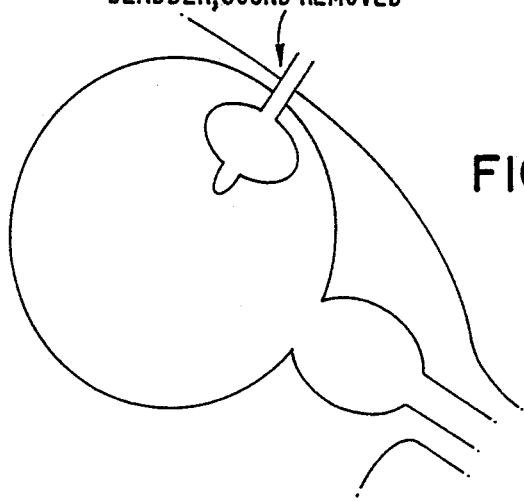

Once the apparatus and catheter are coupled, the assembly is pulled into the bladder and through the urethra to the extent that the catheter tip may be disengaged from the second end of the elongate element. Once the catheter is disengaged, the catheter is drawn back through the urethra and positioned within the bladder as shown in FIG. 11.

It should be understood that the foregoing description of my invention has been illustrated merely by example and such description should not be interpreted as being restrictive in any way. Obvious changes in its construction will be apparent to one skilled in the art and such changes are intended to be encompassed by this inventive description.

I claim:

1. A surgical apparatus for placement of a suprapubic catheter within the bladder of a patient by a surgical procedure which involves inserting an end of the surgical apparatus through the urethra of the patient into the bladder, making an incision through the abdomen and bladder, pushing the end of the apparatus out through the incision, releasably coupling the end of the apparatus to a catheter, pulling the coupled apparatus and catheter into the bladder, releasing the catheter from the apparatus in the bladder and withdrawing the apparatus out of the patient, said apparatus, comprising:

an elongate element defining a hollow tube having a gripping portion for gripping and manipulating the apparatus and a curved portion for insertion through the urethra into the bladder of the patient, said gripping portion terminating in a first end and said insertion portion terminating in a second end, a flexible wire disposed within said elongate element, said flexible wire having first and second ends corresponding to said first and said second ends of said elongate element and having a length substantially extending from said first end to said second end of said elongate element, said second end of said flexible wire including a coupling portion which can be inserted through an opening in a catheter tip to releasably couple said flexible wire to the catheter tip, and a means for reciprocating said flexible wire within said elongate element, said reciprocating means including a handle operatively connected to said first end of said flexible wire, so that when said handle is in a first position, said second end of said flexible wire projects from said second end of said elongate element for coupling with the catheter tip, and when said handle is in a second position, said second end of said flexible wire and the catheter tip are retracted within said second end of said elongate element.

2. The surgical apparatus according to claim 1, wherein said coupling is a hook.

3. The surgical apparatus according to claim 1, further comprising a removable cap for covering said second end of said elongate element, said removable cap having a blunt tip portion and a rear portion engageable with said second end of said elongate element.

4. The surgical apparatus according to claim 3, wherein said coupling of said flexible wire is a hook, and wherein said rear portion of said removable cap has an opening for passing therethrough said hook for coupling said removable cap to said elongate element.

5. The surgical apparatus according to claim 1, wherein said elongate element is provided with a recessed inner end wall disposed within said elongate element at said second end, said recessed inner end wall having a slot for passing therethrough said flexible wire.

6. The surgical apparatus according to claim 1, wherein said reciprocating means is a spring disposed within said elongate element, so that when said handle is in the first position, said spring is compressed and said second end of said flexible wire projects from said second end of said elongate element for coupling with the catheter tip, and when said handle is in the second position, said spring is uncompressed and said second end of said flexible wire and the catheter tip are retracted within said second end of said elongate element.

7. The surgical apparatus according to claim 1, wherein said reciprocating means is a spring disposed outside of said elongate element at said first end of said elongate element, so that when said handle is in the first position, said spring is compressed and said second end of said flexible wire projects from said second end of said elongate element for coupling with the catheter tip, and when said handle is in the second position, said spring is uncompressed and said second end of said flexible wire and the catheter tip are retracted within said second end of said elongate element.

* * * * *